United States Patent [19]

Tang et al.

[11] Patent Number: 6,066,314
[45] Date of Patent: May 23, 2000

[54] ANTIPERSPIRANT ACTIVES AND FORMULATIONS MADE THEREFROM

[75] Inventors: Xiaozhong Tang, Piscataway; Kathy Potechin, Short Hills; Jairajh Mattai, Piscataway; Anthony Esposito, Roselle; Paul Joseph Vincenti, Jefferson, all of N.J.

[73] Assignee: Colgate-Palmolive Company, New York, N.Y.

[21] Appl. No.: 09/432,462

[22] Filed: Nov. 3, 1999

Related U.S. Application Data

[62] Division of application No. 08/959,874, Oct. 29, 1997.
[51] Int. Cl.⁷ .............................. A61K 7/32; A61K 7/34; A61K 7/38; A61K 7/00
[52] U.S. Cl. ............................ 424/65; 424/66; 424/68; 424/400; 424/401
[58] Field of Search .................... 424/65, 66, 68, 424/400, 401

[56] References Cited

U.S. PATENT DOCUMENTS

| | | | |
|---|---|---|---|
| 4,017,599 | 4/1977 | Rubino | 424/65 |
| 4,359,456 | 11/1982 | Gosling et al. | 424/68 |
| 4,435,382 | 3/1984 | Shin et al. | 424/66 |
| 5,225,187 | 7/1993 | Carmody | 424/66 |
| 5,500,209 | 3/1996 | Ross et al. | 424/66 |
| 5,518,714 | 5/1996 | Park | 424/65 |
| 5,547,661 | 8/1996 | Sun et al. | 424/66 |
| 5,589,196 | 12/1996 | Callaghan et al. | 424/617 |
| 5,596,729 | 1/1997 | Barr et al. | 424/68 |
| 5,643,558 | 7/1997 | Provancal et al. | 424/66 |
| 5,997,850 | 12/1999 | Tang et al. | 424/65 |

*Primary Examiner*—Shelley A. Dodson
*Attorney, Agent, or Firm*—Rosemary M. Miano

[57] ABSTRACT

The present invention comprises stabilizing aqueous solutions of aluminum zirconium based salts with a water soluble amino acid, especially glycine, wherein the Zr:glycine weight ratios used to form solutions of the active itself or used to form cosmetic compositions made according to this invention are in the range from 1:1.2 to 1:5, particularly 1:2 to 1:4, and more particularly in the range of 1:2 to 1:3 on a weight:weight basis. By reducing the polymerization of small zirconium species with an elevated amount of amino acid(s), the efficacy of the antiperspirant salt is maintained.

14 Claims, 6 Drawing Sheets

ANTIPERSPIRANT ACTIVES AND FORMULATIONS MADE THEREFROM

This is a divisional of the prior application Ser. No. 08/959,974 filed Oct. 29, 1997, which application is now granted and is hereby incorporated by reference.

FIELD OF THE INVENTION

The present invention concerns the stabilization of small zirconium species in aqueous solutions of aluminum zirconium glycine salts (ZAG) and compositions made therewith such as antiperspirants. Current commercial ZAG salts contain glycine as a buffering agent, and the glycine/Zr weight ratio is approximately 1:1. However, in aqueous solution, such as in the aqueous phase of an antiperspirant gel product, polymerization of zirconium occurs over time, thus reducing efficacy. The present invention provides a method for improving the stabilization of such solutions. The polymerization of zirconium in aqueous solutions of ZAG is significantly reduced over time by increasing the amount of an amino acid, such as glycine, to prevent the formation of higher molecular weight zirconium species.

BACKGROUND OF THE INVENTION

Antiperspirant salts, such as aluminum chlorohydrex (also called aluminum chlorohydrex polymeric salts and abbreviated here as "ACH") and aluminum zirconium glycine salts (abbreviated here as "ZAG", "ZAG complexes" or "AZG"), are known to contain a variety of polymeric and oligomeric species with molecular weights (MW) ranging from 100–500,000. It has been clinically shown that, in general, the smaller the species, the higher the efficacy on sweat reduction. A number of efforts have focused on (1) how to select the components of ACH and ZAG which affect the performance of these materials as antiperspirants and deodorants and (2) how to manipulate these components to obtain and maintain the presence of smaller types of these components.

These attempts have included the development of analytical techniques. Size exclusion chromatography ("SEC") or gel permeation chromatography ("GPC") are methods frequently used for obtaining information on polymer distribution in antiperspirant salt solutions. With appropriate chromatographic columns, at least five distinctive groups of polymer species can be detected in a ZAG, appearing in a chromatogram as peaks 1, 2, 3, 4 and a peak known as "5,6". Peak 1 is the larger Zr species (greater than 120–125 Å). Peaks 2 and 3 are larger aluminum species. Peak 4 is smaller aluminum species (aluminum oligomers) and has been correlated with enhanced efficacy for both ACH and ZAG salts. Peak 5,6 is the smallest aluminum species. The relative retention time ("Kd") for each of these peaks varies depending on the experimental conditions.

Various analytical approaches for characterizing the peaks of ACH and various types of ZAG actives are found in "Antiperspirant Actives—Enhanced Efficacy Aluminum-Zirconium-Glycine (AZG) Salts" by Dr. Allan H. Rosenberg (*Cosmetics and Toiletries Worldwide,* Fondots, D. C. ed., Hartfordshire, UK: Aston Publishing Group, 1993, pages 252, 254–256). Using GPC, Rosenberg describes four peaks identified as AlKd 0.0; 0.24; 0.40; and 0.60. Activated ACH is identified as material having an enriched AlKd0.4 content. Rosenberg points out that activated AZG salts with enriched AlKd0.4 content do not necessarily give enhanced performance in antiperspirant use and notes that zirconium polymer distributions are more important than AlKd0.4 enrichment in predicting clinical efficacy, with lower molecular weight zirconium polymer distributions being more desirable.

Attempts to obtain antiperspirant salts with improved efficacy have included developing processes for obtaining better types of ACH such as by heating solutions of ACH with or without elevated pressure in order to depolymerize larger species into peak-4 species. Examples can be found in U.S. Pat. No. 4,359,456 to Gosling et al. Since ACH solutions may be used as starting materials for aluminum zirconium glycine (ZAG or AZG) salts, heating ACH solutions has also been used to enrich peak-4 oligomers before spray drying. Such an approach does not, however, directly address the issue of zirconium species.

U.S. Pat. No. 4,775,528 to Callaghan et al describes the formation of a solid antiperspirant composition having an Al:Zr atomic ratio from 6:1 to 1:1; the GPC profile of the antiperspirant in solution gave a ratio of at least 2:1 for peak 4/peak 3. This reference specifies that the zirconyl hydrochloride be mixed with the aluminum chlorhydroxide solution before the drying step is completed. The emphasis is placed on optimizing the aluminum chemistry and there is no discussion of any effects on the zirconium chemistry.

There have been some previous attempts at using glycine in antiperspirant salts. For example, European patent Application 0 499 456 A2 assigned to Bristol-Myers Squibb Company describes a ZAG complex and a process for making the complex comprising mixing zirconium hydroxychloride, a selected aluminum chloro species and an amino acid in aqueous solution and, optionally drying the aqueous solution to obtain a dry ZAG salt.

U.S. Pat. No. 4,435,382 to Shin et al teaches the complexing of aluminum/zirconium salts with glycine to alter the solubility of such salts in an anhydrous alcoholic vehicle to render the salts less soluble and more readily suspended therein.

U.S. Pat. No. 5,518,714 to Park discloses antiperspirants particularly suitable for roll-on products wherein the dissolution of the antiperspirant active in anhydrous ethanol or isopropanol can be inhibited by including a compound selected from those having a basic nitrogen function (such a glycine).

U.S. Pat. No. 4,871,525 to Giovanniello et al describes an aluminum zirconium hydroxyl halide glycinate complex having improved antiperspirant activity wherein the glycine is used to prevent gel formation. The ratio of Zr to glycine is less than 1:1 (see column 5, lines 36–39).

U.S. Pat. No. 5,225,187 to Carmody teaches a process for preparing concentrated aluminum/zirconium/glycine solutions which can produce a solution having 45–50% solids. The ratio of Zr to glycine is in the range of 0.8–1–1.2:1 (see column 3, lines 64–66).

U.S. Pat. No. 5,589,196 to Callaghan et al discloses an antiperspirant composition including zirconyl hydroxy chloride and aluminum chlorhydroxide which can contain a neutral amino acid such as glycine in an amount of 1:1 glycine to zirconyl hydroxy chloride.

U.S. Pat. No. 5,643,558 to Provancal et al teaches a process for preparing an enhanced efficacy aluminum/zirconium antiperspirant salt in a polyhydric alcohol in which an alkaline glycinate salt may be added to the polyhydric alcohol prior to the addition of the salt to raise the pH of the recovered product. This zinc glycinate is in addition to any glycine present in the Al/Zr salt. European Patent Application 0 047 650 A2 assigned to the Procter & Gamble Company discloses an antiperspirant composition obtained by forming a water-soluble, stable complex including a combination of an aluminum compound, a zirconium compound, a neutral amino acid and an inorganic acidic compound. The amino acid is present in a minor proportion.

European Patent Application EP 0 653 203 A1 to Rosenberg et al describes a process for making ZAG salt with high antiperspirant activity. According to this reference, glycine is added to Zr starting materials at ambient temperature, and the mixed Zr/glycine is admixed with the aluminum chlorohydrate starting material immediately prior to spray drying in a continuous or semi-continuous operation.

Spray drying AZG within a prescribed time frame to fix the desired distributions of the 4 peaks in a powder has also been suggested. See Rosenberg, A., "New Antiperspirant Salt Technology" (*Cosmetics and Toiletries Worldwide*, Fondots, D. C. ed., Hartfordshire, UK: Aston Publishing Group, 1993, pages 214–218).

Previous processes for making active salts generally include a method described by the following Reaction Scheme I:

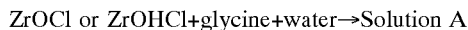
ZrOCl or ZrOHCl+glycine+water→Solution A

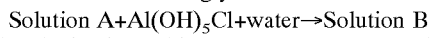
Solution A+Al(OH)$_5$Cl+water→Solution B

The glycine is used in an amount up to a Zr/glycine ratio of 1:1. Solution B is then immediately spray dried to obtain the final powder form of the active salt. Such processes may produce ZAG salts with more small Zr polymer species in powder form; however, stabilizing small Zr polymer species, in high concentration aqueous solutions (above 10% weight/weight) (for example, in the range of 10–50% by weight based on the total weight of the solution) over prolonged periods of time, still remains a challenge.

Thus, it is an object of the invention to stabilize small zirconium species in an aqueous solution of ZAG wherein the aqueous solution of these salts will have a reduced formation of higher molecular weight zirconium species. It is a further object to provide aluminum zirconium glycine solutions which have enhanced stability by the use of an amino acid such as glycine in an amount which is greater than 1:1 Zr:amino acid. It is another object of the invention to provide aluminum zirconium glycine solution which can be formulated into cosmetic products having improved efficacy and increased shelf-life. It is another object of the invention to provide a process for producing aluminum zirconium-glycine solutions which have improved efficacy in antiperspirant and/or deodorant compositions and which do not require an immediate spray drying step. It is still a further object of the invention to provide an improved method for characterizing the zirconium species present in aqueous solutions, especially aqueous solutions of ZAG. These and other objects of the invention will be apparent from the following description.

SUMMARY OF THE INVENTION

The present invention comprises stabilizing aqueous solutions of aluminum zirconium based salts with an amino acid, especially glycine, (or mixture of amino acids) in a selected ratio of zirconium:amino acid. Further dilutions of the aqueous solution may be made (for example, with water) which retain stability, that is, they exhibit reduced polymerization of small zirconium species as evaluated after some period of time. The amino acid can also be added to an aqueous solution having a zirconium component, such as ZrOCl$_2$ and/or ZrO(OH)Cl, admixed with an ACH which itself has an enhanced content of smaller aluminum species, during the synthesis of the ZAG solution. In any case, the final Zr:glycine weight ratios used to form solutions of the active itself or used to form cosmetic compositions made according to this invention are in the range of 1:1.2 to 1:5, more particularly 1:2 to 1:4, and especially in the range of 1:2 to 1:3. By reducing the polymerization of small zirconium species with an elevated amount of amino acid(s), the efficacy of the antiperspirant salt is maintained. Further, the shelf-life and efficacy of antiperspirant products containing ZAG solutions may also be enhanced.

DETAILED DESCRIPTION OF THE INVENTION

Figure 1:
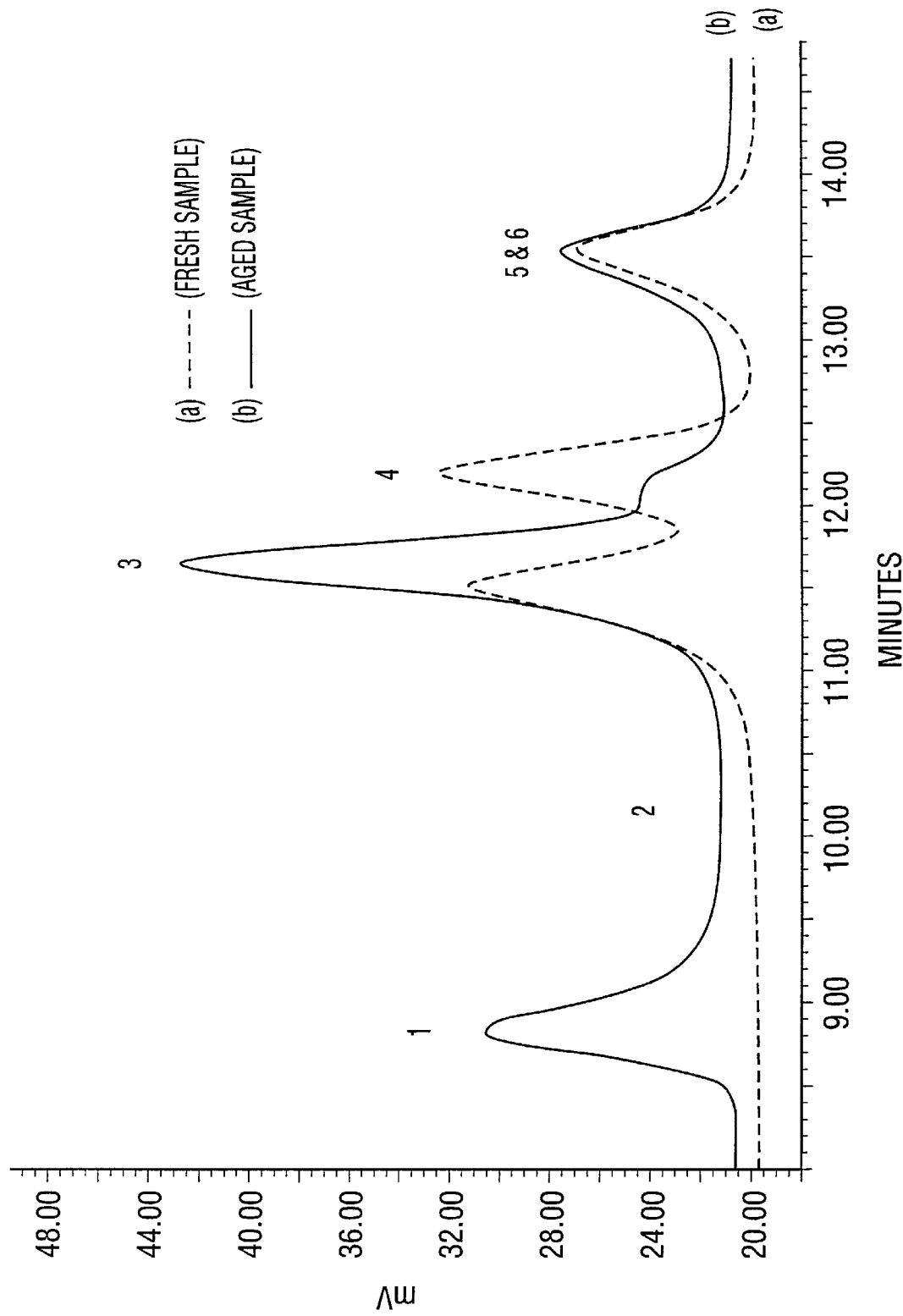
FIG. 1 shows GPC profiles for solutions of a particular ZAG (Q5-7167 AAZG from Summit Research Labs, Somerset, N.J.). Chromatogram (a) shows a GPC profile of a fresh solution of a ZAG. Chromatogram (b) shows the same sample after 1 month of aging at room temperature.

The present invention is directed to a method of stabilizing aqueous solutions of aluminum zirconium salts such as aluminum zirconium glycine salts (ZAG) and cosmetic compositions formed therewith wherein the Zr: amino acid weight ratio is in the range of 1:1.2 to 1:5, more particularly 1:2 to 1:4, and especially in the range of 1:2 to 1:3. The invention also comprises solutions and cosmetic compositions made by such method. The method includes adding at least one amino acid to an aqueous solution comprising zirconium either before or after the solution is made.

By stabilized is meant that the composition formed with the additional amino acid retains approximately the same amount of the smaller zirconium species present in the initial sample as evaluated by GPC after at least 30 days aging at room temperature.

The types of aluminum zirconium based salts that may be used in this invention include those which are commonly considered antiperspirant active materials and which contain zirconium. These by way of example (and not of a limiting nature), zirconyl hydroxychloride, aluminum zirconium glycine complex (for example, aluminum zirconium trichlorohydrex gly, aluminum zirconium pentachlorohydrex gly, aluminum zirconium tetrachlorohydrex gly and aluminum zirconium octochlorohydrex gly) wherein aluminum zirconium tri-, tetra- and penta-chlorohydrate glycine complexes, are coordination complexes of aluminum zirconium tri-, tetra- or penta-chlorohydrate and glycine in which some of the water molecules normally coordinated to the metal have been displaced by the glycine. More particularly, illustrative antiperspirant active metal salts include aluminum zirconium tetrachlorohydrex gly which has an enhanced content of smaller aluminum species; for example, Reach AZP-908 and Reach 902, each manufactured by Reheis Inc., Berkeley Heights, N.J., which are coordination complexes of aluminum zirconium tetrachlorohydrate and glycine in which some of the water molecules normally coordinated to the metal have been displaced by the glycine; and Q5-7167 AAZG from Summit Research Labs, Somerset, N.J. An example of a regular salt not having an enhanced content of smaller aluminum species includes Rezal 36-G a tetra-ZAG salt from Reheis Inc., Berkeley Heights, N.J.).

Even more particular examples of such salts include:

Aluminum Zirconium Tetrachlorohydrex

Reach AZP-701, Reach AZP-902, Reach AZP-908, Reach AZP-255, Reach AZP-855, Rezal-36, Westchlor ZR 35B, Summit AZG-368, Summit AZG-369 Summit AZG-370, Summit Q5-7155 AAZG, and Summit Q5-7167 AAZG.

Aluminum Zirconium Trichlorohydrex

Reach AZZ-902, Reach AZZ-855, Reach AZZ-908, Rezal-33, Westchlor ZR 30B, Westchlor ZR 58B, Westchlor ZR 60B, Summit Q5-7160 AZAG, and Summit AZG5-7164.

Aluminum Zirconium Octachlorohydrex

Reach AZO-902, Reach AZO-908, and Westchlor ZR82B.

Aluminum Zirconium Pentachlorohydrex

Rezal-67 and Westchlor ZR 80B.

Also, corresponding nitrate, bromide and sulfate salts of any of the foregoing may be used.

While examples of salts have been listed, other equivalent salts are also within the spirit and scope of the invention.

While various ranges of antiperspirant salts are described below, it is to be noted that lesser amounts can be used to enhance deodorant activity of deodorant products which are not classified as antiperspirants.

Examples of suitable amino acids which may be added to the aluminum/zirconium salt in the ratios described herein are glycine, alanine, threonine and leucine, especially glycine. Preferably the amino acids used are water soluble. Mixtures of amino acids may also be used. The solutions and products made therefrom exhibit increased stability of small zirconium species in aqueous environments, thus maintaining efficacy and increasing the shelf life of products such as antiperspirants and deodorants made therefrom.

Glycine is known to prevent gelling of Al—Zr salts in aqueous solution (see EP 0 653 203 A1) and also to function as a buffering agent to maintain a pH of around 3 to prevent skin irritation. Glycine forms a complex with Zr:

In aqueous solution only about 50–75% of glycine is bound to Zr while 100% glycine is bound to Zr in the powder form. Therefore, in an aqueous solution of a typical ZAG, the Zr/glycine interaction can be represented by the following equilibrium:

It is believed that the additional amount of amino acid, such as glycine or other water soluble amino acids, shifts the equilibrium to the left. By complexing the zirconium, it is believed that the amino acids retard the polymerization of free zirconium to larger (and undesirable) molecular weight species.

While specific ranges have been described for Zr:amino acid ratios, it is to be noted that for a particular ZAG and a particular amino acid, it is advisable to optimize the exact ratio for that individual system.

It should also be noted that the polymers described in this application do not have discrete values for molecular weight, but rather have a weight average value.

The classical method of synthesizing ZAG salts is to react an aluminum component such as ACH with a zirconium component such as $ZrOCl_2$ and/or $ZrO(OH)Cl$ and glycine in a single step with heating, followed by spray drying, to obtain the ZAG salt in a powder form. This procedure can be used to prepare tri-, tetra, penta- and octa- ZAG salts. The glycine to Zr molar ratio is between 1 and 3. However, this process gives rise to large zirconium polymers having reduced efficacy.

An advance in this basic methodology to obtain more efficacious ZAG salt is disclosed in EP 0 653 203 A1 whereby the zirconium species is admixed with the glycine in an aqueous environment followed by admixture with the aluminum salt. No heat is used in this process. The final mixture is spray dried to obtain the ZAG salt in a powder form. Even with this methodology, polymerization of zirconium occurs in aqueous solution (see FIG. 1, chromatograms (a) and (b)).

The method of the present invention is accomplished by adding sufficient amino acid (or mixtures thereof) to an aluminum/zirconium composition or solution thereof so that the level of added amino acid to aluminum/zirconium composition is in a ratio in the range of 1:1.2 to 1:5, more particularly 1:2 to 1:4, and especially in the range of 1:2 to 1:3 for Zr:amino acid. The amino acid, preferably glycine, can be directly added as a solid to the ZAG in solution. This method may be accomplished in a number of ways. For example, a 40% solution of the ZAG can be prepared in distilled water (40.0 g ZAG+60.0 g water). The glycine, as a powder, can be added directly to this solution, with stirring at room temperature for 1–2 minutes. Specific examples will be discussed in detail in later sections.

Alternatively, the glycine can be added directly during the manufacture of ZAG. For example, a zirconium component, such as zirconium oxychloride ($ZrOCl_2$) and/or zirconium hydroxychloride $ZrO(OH)Cl$, in aqueous solution, can be admixed with an ACH. Glycine, as a powder, can then be added to this solution in the amounts as described earlier. In this process, the spray drying step can be eliminated.

Analytical Methods

GPC-ICP can be used to investigate whether zirconium and aluminum species co-elute at similar retention times or elute separately from the column at different retention times. The ICP unit is directly coupled to the GPC unit as a detector so that the oligomeric fractions separated by the GPC column are elucidated on-line quantitatively for Al, Zr and other elements. The ICP's detector is a simultaneous charge induction device (CID) with a wavelength of 175 to 800 nm. The eluent from the GPC column is analyzed and a data point is noted about once every six seconds for Al and Zr. The data points collected are plotted against retention time, to form the chromatogram for each element separately. The number for the individual peak areas represents the relative concentration for that specific element.

The method of characterizing and monitoring the zirconium and aluminum content and species in an aqueous solution of zirconium and aluminum, especially ZAG solutions, may be done by combining GPC and ICP. This is useful to investigate whether zirconium and aluminum species co-elute at similar retention times or elute separately from the column at different retention times. In one method the GPC column separates the species by molecular size, using a refractive index (RI) detector connected to the column outlet. The eluent fractions from the GPC are evaluated further by analysis of the individual fractions by ICP. In a second method, (which is used in some of the examples below), GPC may be directly coupled to ICP. The eluent fractions passing through the column are directly linked to the ICP unit; the ICP unit in this case is used as a detector. Data points are collected such as, for example, one data point every 6 seconds. For either of these methods data my be plotted and the presence of small Zr species monitored.

Any antiperspirant and/or deodorant products (collectively referred to as "underarm products" or "products for reducing malodor"), which contains the ZAG salts in an aqueous phase, can be made with the stabilized ZAG materials of this invention. These products can include any forms which have a water component such as sticks, gels, soft solids and creams. Illustratively, antiperspirant product compositions according to the present invention contain the antiperspirant active material in an amount of 10–30% by weight, of the total weight of the composition.

The compositions according to the present invention can also include other, optional, components conventionally incorporated in antiperspirant stick compositions, including (but not limited to) additional emollients, detackifiers, perfumes (fragrances), antibacterial agents, fangistats, pigments (such as opacifiers), dyes, colorants, ultraviolet absorbers (sunscreens), insect repellents, etc. Illustratively, and not limiting, the perfumes normally employed in cosmetic compositions can be employed in compositions of the present invention, if desired, with concentrations of such perfumes typically being up to about 2%, e.g., about 0.5% to 2%, by weight, of the total weight of the composition.

An illustrative antibacterial agent that can be utilized according to the present invention is Triclosan; benzethonium chloride; zinc phenolsulfonate, and Triclocarban. Typically compositions according to the present invention may contain up to about 2% antibacterial agents, preferably about 0.1% to 1.5%, by weight, of the total weight of the composition.

Examples of formulations of sticks that can be made with compositions of the present invention include combining the appropriate ingredients by conventional techniques. The percents given below are weight percents based on the total weight of the composition.

Antiperspirant Stick "A"

Oil Phase 1) 0.5–8.0% (preferably 2–6%) of a siloxane polyamide gelling agent such as those described in patent application U.S. Ser. No. 08/904,709, filed Aug. 1, 1997, and incorporated herein by reference in its entirety;

2) 20–60% (preferably 20–60%) of a silicone fluid selected from the group consisting of D4, D5 and D6 cyclomethicones and mixtures thereof where the D# represents the number of siloxane units in the ring;

3) 0–20% (preferably 7–15%) of at least one cosmetic ingredient selected from the group consisting of non-volatile emollients, for example, C8–C22 fatty alcohols, C12–C36 fatty esters, C8–C18 alkyl benzoates, and linear polysiloxanes;

4) 0–10% (preferably 3–7%) of a cosmetically acceptable surfactant selected from the group consisting of cationic surfactants (for example, cetyltrimethyl ammonium chloride), nonionic surfactants (for example, polysorbate 20), anionic surfactants (for example, sodium lauryl sulfate), amphoteric surfactants (for example, cocamidopropyl hydroxysultaine), dimethicone copolyols and polyether ethoxylates;

5) 0–3% (preferably 1–2%) of a fragrance;

Polar Phase 6) 5–40% (preferably 15–25%) of water and/or water miscible solvents;

7) 1.5–20% (preferably 3–15%) of an amino acid (preferably glycine) or mixtures of amino acids;

8) 10–25% (preferably 15–25%) of a ZAG complex;

9) 0–5% (preferably 1–2%) of a cosmetically acceptable surfactant selected from the group consisting of cationic surfactants (for example, cetyltrimethyl ammonium chloride), nonionic surfactants (for example, polysorbate 20), anionic surfactants (for example, sodium lauryl sulfate), amphoteric surfactants (for example, cocamidopropyl hydroxysultaine), dimethicone copolyols and polyether ethoxylates.

Antiperspirant Stick "B"

Oil Phase 1) 20–60% (preferably 25–40%) of a cosmetically acceptable solvent, for example, a member selected from the group consisting of C2–C8 polyhydric alcohols (especially dihydric), C8–C22 unsaturated fatty alcohols, and branched and straight chain C8–C22 saturated fatty alcohols;

2) 0–10% (preferably 4–9%) of a cosmetically acceptable surfactant selected from the group consisting of cationic surfactants (for example, cetyltrimethyl ammonium chloride), nonionic surfactants (for example, polysorbate 20), anionic surfactants (for example, sodium lauryl sulfate), amphoteric surfactants (for example, cocamidopropyl hydroxysultaine), dimethicone copolyols and polyether ethoxylates;

3) 0–3% (preferably 1–2%) of a fragrance;

4) 5–25% (preferably 10–20%) of a linoleic acid dimer based polyamide as described in U.S. Pat. No. 5,500,209 and incorporated by reference herein;

Polar Phase 5) 5–40% (preferably 15–25%) of water and/or water miscible solvents;

6) 1.5–20% (preferably 3–15%) of an amino acid (preferably glycine) or mixtures of amino acids;

7) 10–25% (preferably 15–25%) of a ZAG complex;

8) 0–5% (preferably 1–2%) of a cosmetically acceptable surfactant selected from the group consisting of cationic surfactants (for example, cetyltrimethyl ammonium chloride), nonionic surfactants (for example, polysorbate 20), anionic surfactants (for example, sodium lauryl sulfate), amphoteric surfactants (for example, cocamidopropyl hydroxysultaine), dimethicone copolyols and polyether ethoxylates.

Examples of formulations of gels that can be made with compositions of the present invention include a transparent antiperspirant gel made by combining:

Gel

Oil Phase
1) 5–20% (preferably 7–12%) cyclomethicone;
2) 0.5–2% (preferably 0.8–1.5%) dimethicone copolyol;
3) 5–20% (preferably 7–12%) linear silicones (for example, dimethicone);

Polar Phase
4) 25–60% (preferably 30–45%) water;
5) 5–40% (preferably 7–30%) water miscible solvents;
6) 1.5–20% (preferably 3–15%) of an amino acid (preferably glycine) or mixtures of amino acids;
7) 10–25% (preferably 15–23%) of a ZAG complex;
8) 0–2% (preferably 0.5–1%) of a cosmetically acceptable surfactant selected from the group consisting of cationic surfactants (for example, cetyltrimethyl ammonium chloride), nonionic surfactants (for example, polysorbate 20), anionic surfactants (for example, sodium lauryl sulfate), amphoteric surfactants (for example, cocamidopropyl hydroxysultaine), dimethicone copolyols and polyether ethoxylates.

Examples of formulations of creams that can be made with compositions of the present invention include creams made by combining:

Cream

Oil phase
1) 2–10% (preferably 3–6%) Cyclomethicone;
2) 0.1–3% (preferably 0.4–1.0%) of triglycerides such as mono-, di-, or triglycerides and mixtures thereof (for example, glycerol monostearate);
3) 4–15% (preferably 8–12%) cosmetically acceptable surfactants/emulsifiers (for example a member selected from the group consisting of cationic surfactants (for example, cetyltrimethyl ammonium chloride), nonionic surfactants (for example, polysorbate 20), anionic surfactants (for example, sodium lauryl sulfate), amphoteric surfactants (for example, cocamidopropyl hydroxysultaine), dimethicone copolyols and polyether ethoxylates;
4) 3–8% (preferably 3.5–6.5%) of a C8–C22 fatty alcohol;

Polar Phase
5) 40–89% (preferably 50–70%) water;
6) 1.5–20% (preferably 3–15%) amino acid (preferably glycine);
7) 10–25 (preferably 15–25%) ZAG complex.

Examples of sprays that can be made with the compositions of the present invention include a water-based pump spray made by combining:

Spray 1) 35–87% (preferably 53%–75%) water;
2) 3–7% (preferably 4–5%) water soluble emollient;
3) 0.5–3% (preferably 1–2%) of a cosmetically acceptable surfactant selected from the group consisting of cationic surfactants (for example, cetyltrimethyl ammonium chloride), nonionic surfactants (for example, polysorbate 20), anionic surfactants (for example, sodium lauryl sulfate), amphoteric surfactants (for example, cocamidopropyl hydroxysultaine), dimethicone copolyols and polyether ethoxylates;
4) 10–25% (preferably 15–25%) of a ZAG;
5) 1.5–20% (preferably 3–15%) of an amino acid (preferably glycine) or mixtures of amino acids.

Examples of a water based roll-on that may be made with the compositions of the present invention include a composition made by combining:

Roll-on 1) 27–89% (preferably 45–70%) water;
2) 0.5–3% (preferably 1–2%) of magnesium aluminum silicate;
3) 0.5–10% (preferably 3–7%) of a cosmetically acceptable surfactant selected from the group consisting of cationic surfactants (for example, cetyltrimethyl ammonium chloride), nonionic surfactants (for example, polysorbate 20), anionic surfactants (for example, sodium lauryl sulfate), amphoteric surfactants (for example, cocamidopropyl hydroxysultaine), dimethicone copolyols and polyether ethoxylates;
4) 0–5% (preferably 1–2%) of water miscible solvent(s);
5) 10–25% (preferably 15–25%) of a ZAG;
6) 1.5–20% (preferably 3–15%) of an amino acid (preferably glycine) or mixtures of amino acids.

Examples of water-in-silicone antiperspirant roll-ons are those made by combining:

Oil Phase
1) 20–50% (preferably 25–35%) cyclomethicone;
2) 0.5–2% (preferably 0.8–1.5%) dimethicone copolyol;

Polar Phase
3) 30–50% (preferably 38–45%) water;
4) 5–40% (preferably 15–25%) water miscible solvents;
5) 1.5–20% (preferably 3–15%) of an amino acid (preferably glycine) or mixtures of amino acids;
6) 10–25 (preferably 15–25%) of a ZAG complex;
7) 0–2% (preferably 0.5–1%) of a cosmetically acceptable surfactant selected from the group consisting of cationic surfactants (for example, cetyltrimethyl ammonium chloride), nonionic surfactants (for example, polysorbate 20), anionic surfactants (for example, sodium lauryl sulfate), amphoteric surfactants (for example, cocamidopropyl hydroxysultaine), dimethicone copolyols and polyether ethoxylates.

EXAMPLES

The following Examples illustrate the invention described herein but should not be construed as limitations thereon. Unless otherwise indicated, chemical and scientific terms and abbreviations used throughout this application have their usual and customary meanings. Temperatures are in degrees C., "AP" means antiperspirant active, "gly" means glycine. Unless otherwise stated, all percents described in the Examples and elsewhere in this application are in weight percents based on the total composition as 100%.

Example 1

Analytical Technique for Monitoring Zr Species of Peak 1

Figure 2:
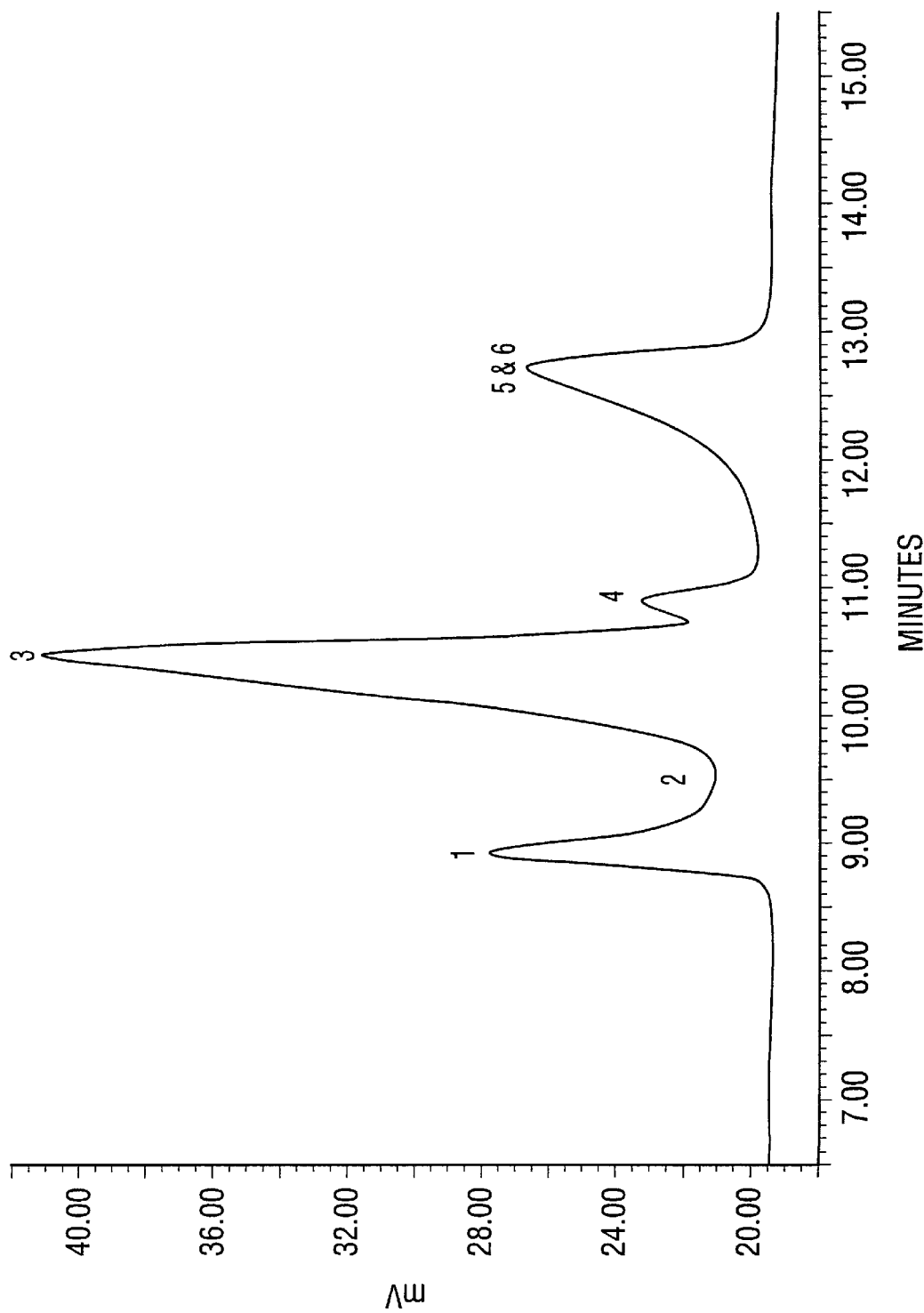
FIG. 2 is a GPC chromatogram of a solution of ZAG (Rezal 36-G from Reheis Inc., Berkeley Heights, N.J.).
Figure 3:
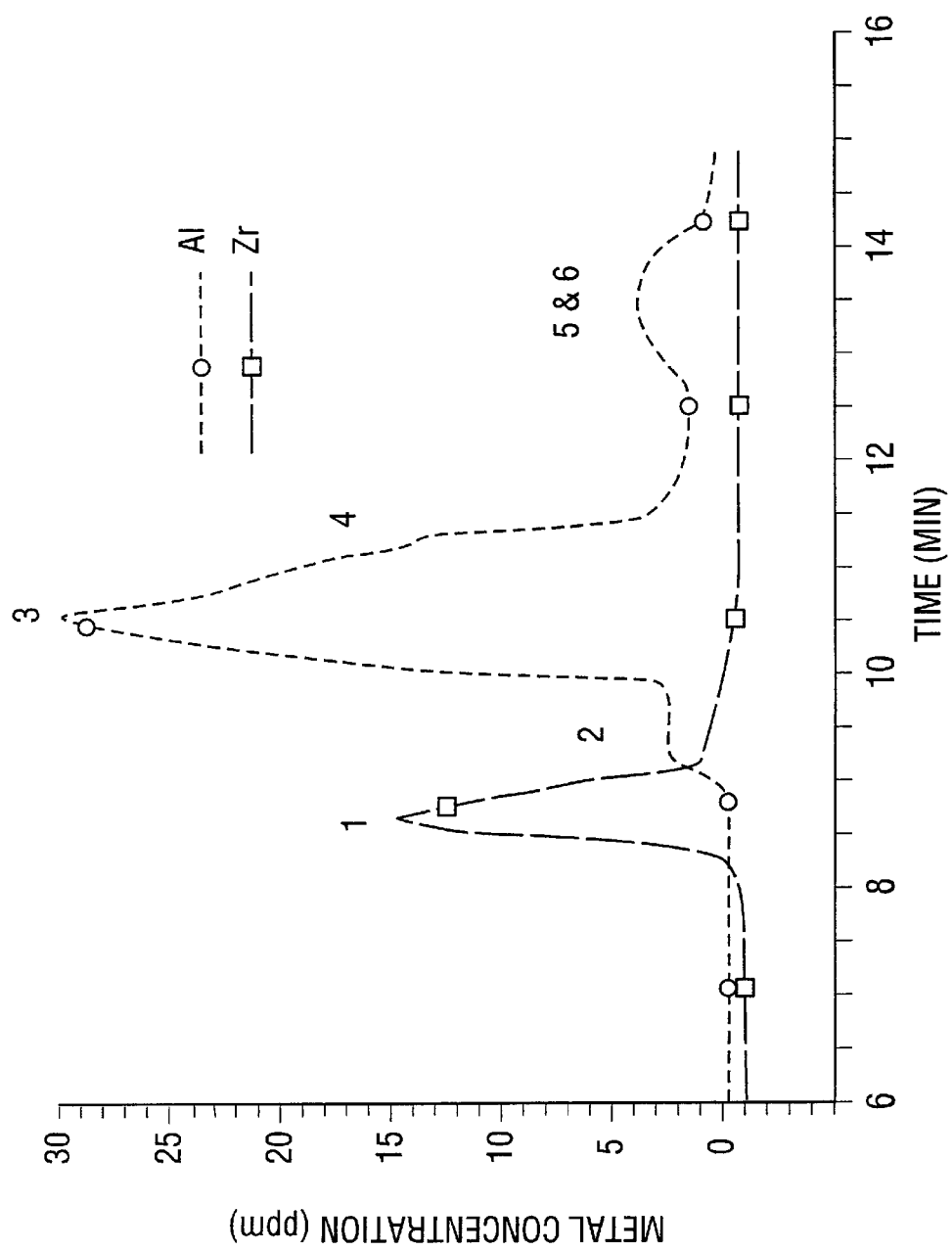
FIG. 3 is an ICP profile of the ZAG described in FIG. 2 (Rezal 36-G) after eluting from the GPC column.

A fifty two percent solution of a ZAG salt (Rezal 36-G, Reheis Inc., Berkeley Heights, N.J.; Zr/glycine weight ratio approximately 1:1), is prepared in distilled water. This is done by adding 48.0 g of water to 52.0 g of the ZAG salt with stirring at room temperature for about 5 minutes. This solution is further diluted to a 10% solution (19.23 g of the 50% solution+80.77 g water) for GPC analysis. The chromatogram is run using the following parameters: Waters® 600 analytical pump and controller, Rheodyne® 7725I injector, Protein-Pak® 125 (Waters) column, Waters 410 Differential Refractometer detector, 5.56 mM nitric acid mobile phase, 0.70 ml/min flow rate, 2.0 microliter injection volume. Data was analyzed using Waters® millenium 2.1 software (Waters Corporation, Milford, Mass.). In order to investigate whether zirconium and aluminum species co-elute at similar retention times or elute separately from the column at different retention times, GPC was coupled to ICP (unit obtained from Thermal-Jarrel-Ash, Inc., Franklin, Mass.). The ICP unit is connected to the GPC unit as a detector so that the oligomeric fractions separated by the GPC column is elucidated on-line quantitatively for Al, Zr and other elements. The eluent from the GPC column is analyzed once every 6 seconds for Al and Zr. The ICP's detector is a simultaneous charge induction device (CID) with a wavelength of 175 to 800 nm. The data points collected are plotted against retention time, to create a chromatogram for each element separately. FIG. 2 shows a GPC chromatogram of Rezal 36G. For each trace 5 peaks are shown, each identified by their retention times (RT) as follows: peak 1 (Kd=0), peak 2 (Kd=0.05), peak 3 (Kd=0.20 ), peak 4 (Kd=0.33 ) and peak 5 & 6 (Kd=0.53). FIG. 3 shows the ICP profile for Rezal 36G. Peak 1 of the GPC profile is identified as exclusively oligomeric and polymeric zirconium species, while peaks 3, 4, and 5, 6 are identified as aluminum species.

Example 2

Preparation of Stabilized ZAG Salt With Glycine

One method of how a stabilized ZAG salt with additional glycine can be made is as follows. Glycine powder (78.0 g) is added to a zirconium compound (262.1 g of a 26% solution of zirconium hydroxychloride (ZrO(OH)Cl) or 245.2 of a 31% solution of zirconium oxychloride (ZrOCl$_2$)) with stirring. ACH (270.0 g of a 50% aqueous ACH solution) is then added with additional stirring. The final zirconium:glycine ratio is 1:2.

Example 3

A forty six percent solution of a ZAG salt (Q5-7167 AAZG), as described above, manufactured using the procedure documented in EP 0 653 203 A1; the Zr/glycine weight ratio approximately 1:1) was prepared in distilled water by adding 54.0 g of water to 46.0 g of the ZAG salt with stirring for 5 minutes at room temperature. This solution was further diluted to 10% for GPC analysis by adding 7.83 g of water to 2.17 g of ZAG solution. FIG. 1, chromatogram (a) shows the GPC chromatogram of the solution. The chromatogram shows small sizes for peaks 1 and 2; however, there are significant sizes for peaks 3, 4, and 5, 6. The small size of peak 1 together with the significant size of peak 4 are predicted to enhance efficacy. FIG. 1, chromatogram (b) shows the chromatogram of Q5-7167 AAZG after 1 month at room temperature. Under these conditions, peak 1 has dramatically increased in area while peak 4 shows significant reduction in area. The cumulative effect of these changes in peak sizes would result in reduced efficacy in solution for the aged Q5-7167 AAZG. Thus, the methods described in EP 0 653 203 A1 for making small zirconium species do not prevent the polymerization of zirconium in solution. As indicated above, aluminum polymerization also occurs on aging; however, as described above, it is believed that the stabilization of zirconium species is a greater contributor to efficacy.

Example 4

Figure 4:
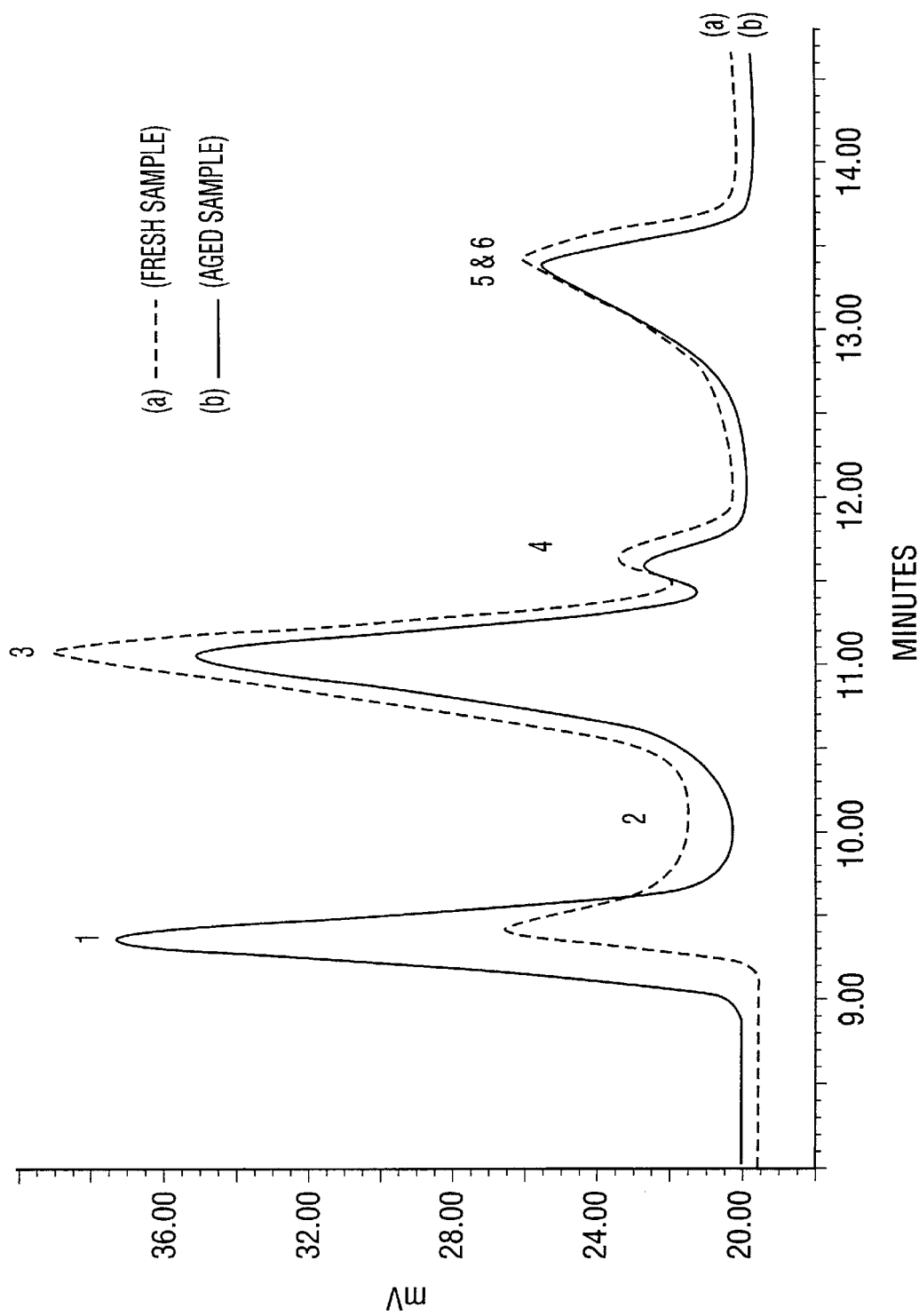
FIG. 4, shows GPC profiles for solutions of a ZAG as described in FIG. 2. Chromatogram (a) shows a GPC profile of a fresh solution of the ZAG. Chromatogram (b) shows the profile after 3 months of aging at room temperature.

A forty six percent solution of a ZAG salt (Rezal 36-G as described in Example 1) in solution was prepared in distilled water using the conditions described above in Example 3. This solution was further diluted to 10% in millipore water (distilled water filtered through a millipore filter) for GPC analysis using the conditions described above in Example 3. FIG. 4, chromatogram (a) shows the GPC chromatogram of a solution made by this method. Table 1 summarizes retention times and peak areas for the four peaks in the GPC chromatogram of Rezal 36-G. Also included in the table are similar parameters for Rezal 36-G after 3 months aging at room temperature (RT). The corresponding chromatogram for aged Rezal 36-G is shown in FIG. 4, chromatogram (b).

TABLE 1

| AP salt | Area Peak 1 (RT = 8.900 min) | Area Peak 3 (RT = 10.95 min) | Area Peak 4 (RT = 11.50 min) | Area Peak 5,6 (RT = 13.48 min) |
|---|---|---|---|---|
| Rezal 36-G (no aging) | 201398 | 672169 | 53806 | 210188 |
| Rezal 36-G (3 months aging) | 372909 | 439443 | 59921 | 209412 |

As indicated above, peak 1 is generated from zirconium oligomers while peaks 3, 4, and "5,6" are from aluminum oligomers. Peaks 1 and 4 are generally correlated with antiperspirant activity; however, peak 1 has a greater correlation with clinical efficacy than peak 4. After 3 months of aging, peak 4 is approximately constant in area while peak 1 has almost doubled in area. The increase in peak 1 area is due to the formation of large oligomeric zirconium species. Since the efficacy of Rezal 36-G is known to decrease with aging, this decrease in efficacy is believed to be primarily due to the formation of large oligomeric zirconium species.

Example 5

Figure 5:
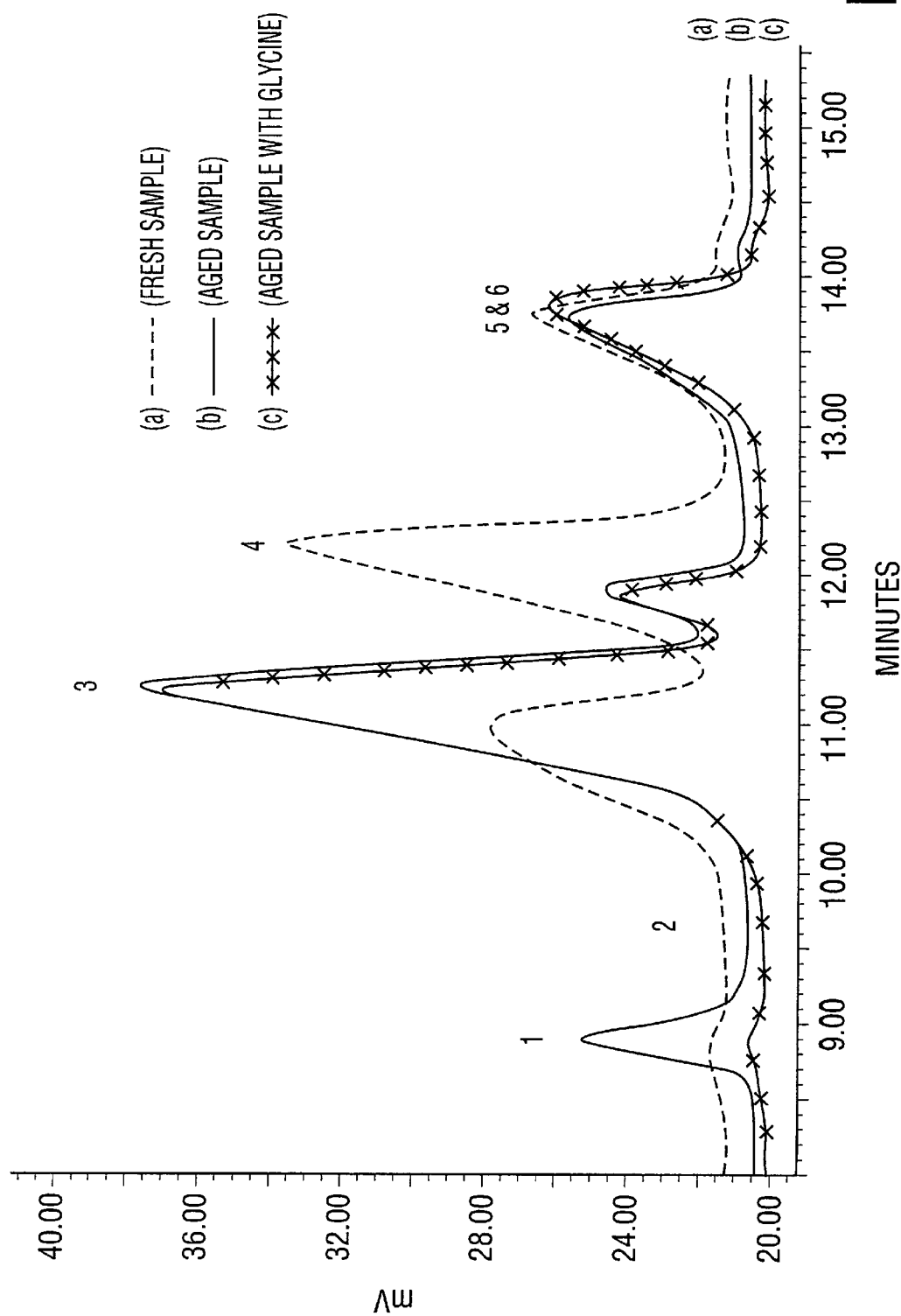
FIG. 5 shows GPC profiles for solutions of a particular ZAG (AZP-902 from Reheis Inc., Berkeley Heights, N.J.). Chromatogram (a) shows the profile of a fresh solution. Chromatogram (b) shows the profile of a sample after 30 days of aging at room temperature. Chromatogram (c) shows the profile a sample after 30 days aging at room temperature with 5% post-added glycine (Zr:glycine ratio of 1:2).

Chromatographic characterization was performed on a ZAG (AZP-902, Reheis Inc.; Zr/glycine weight ratio approximately 1:1), in the presence and absence of 5% post-added glycine. Samples for GPC were prepared from the ZAG salt by first preparing a 50% stock solution in distilled water (weight/weight) by adding 50.0 g of water to 50.0 g of the ZAG salt with stirring at room temperature for about 5 minutes. Water (6.0 g) was added to 24.0 g of this solution to give a 40% solution of the ZAG salt. Additional water (7.5 g) was added to 2.5 g of the 40% solution of ZAG to give a final solution concentration of 10%. A separate set of samples with post-added glycine was prepared by adding 1.50 g glycine to 24.0 g of a 50% solution of the ZAG. The solution was then diluted to 30.0 g with distilled water and hand-shaken for about 1 minute. The final Zr/glycine weight ratio was approximately 1:2. Ten percent solutions of this sample were prepared for GPC analysis by adding 7.5 g water to 2.5 g of the 40% solution of ZAG/glycine mixture. FIG. 5, chromatograms (a), (b) and (c) show GPC profiles for this (a) without aging, (b) after 30 days at room temperature and (c) after 30 days at room temperature with 5% post-added glycine. The corresponding areas of peaks 1 and 4 from the GPC profiles are shown in Table 2.

TABLE 2

| Sample | Zr/glycine ratio | Chromatogram in FIG. 5 | Area Peak 1 | Area Peak 4 |
| --- | --- | --- | --- | --- |
| AZP-902 (no aging) | 1:1 | (a) | 10022 | 387738 |
| AZP-902 (30 days at RT) | 1:1 | (b) | 75630 | 77678 |
| AZP-902 + additional glycine (30 days at RT) | 1:2 | (c) | 10301 | 70429 |

After 30 days at room temperature, the area of peak 1 increased by approximately seven and one-half times over the unaged sample, while that of peak 4 decreased about five-fold from the unaged sample. Both the increase in peak 1 (larger zirconium species) and decrease in peak 4 (reduced quantity of small aluminum species) reduce efficacy of the antiperspirant salt. However, by post-adding glycine to reach a Zr/glycine ratio of 1:2 by weight, the area of peak 1 is unchanged relative to that of the unaged salt. Note that peak 4 is not affected by post-added glycine after aging.

Example 6

The AZP-902/glycine system was further examined by GPC-ICP to determine the percentage of small zirconium species present after aging. In this methodology, GPC-ICP is run without the presence of a column to determine total zirconium content from a 2 microliter injection of a 10% solution of the salt or salt/glycine mixture. GPC-ICP is then run using the Protein Pak® column, as described above in Example 1 and peak 1 is analyzed for zirconium. The Protein Pak® column excludes zirconium species greater than 125 Å and retains species less than 125 Å. Table 3 summarizes the percentage of small zirconium species (less than 125 Å) after 9 weeks aging of AZP-902 solution with and without glycine.

TABLE 3

| Sample | Zr/glycine ratio | % small Zr species |
| --- | --- | --- |
| AZP-902 (no aging) | 1:1 | 56 |
| AZP-902 (aged) | 1:1 | 29 |
| AZP-902 + glycine (aged) | 1:2 | 44 |
| AZP-902 + glycine (aged) | 1:3 | 49 |

The data in Table 3 show that the percentage of small zirconium species increases with the inclusion of additional glycine. The increase is most significant at the Zr/glycine ratio of 1:1 (5% post-addition), and then slowly increases with another 5% glycine addition (Zr/glycine ratio of 1:3). Most importantly, the percentage of small zirconium species after 9 weeks aging in the presence of glycine approaches the percentage for an unaged solution of the salt These results indicate that a solution of AZP-902 will lose efficacy over time. However, by maintaining the baseline value of zirconium oligomers, or alternatively by preventing the polymerization of zirconium to larger species, post-added glycine is able to maintain the efficacy of the antiperspirant. In this Example the protection of peak 1 appears to plateau at a Zr/glycine ratio of 1:3.

Example 7

The effects of other water soluble amino acids (alanine and threonine) in stabilizing small zirconium species were also investigated by GPC. The preparation of these samples is similar to that described in Example 5 using the corresponding amino acids listed in Table 4. Table 4 shows peak 1 areas for solutions of a ZAG, AZZ-902 (Reheis Inc., Zr/glycine weight ratio is 1:1) in the presence and absence of 5 and 10% post added glycine, alanine and threonine, after 2.5 months at room temperature. The zirconium/amino acid weight ratios are 1:1, 1:2 and 1:3.

TABLE 4

| Sample | Post-added amino acid | Zr/amino acid weight ratio | Peak 1 area |
| --- | --- | --- | --- |
| AZZ-902 (no aging) | none | 1:1 | 56245 |
| AZZ-902 (aged) | none | 1:1 | 327733 |
| AZZ-902 (aged) | glycine | 1:2 | 203306 |
| AZZ-902 (aged) | glycine | 1:3 | 135641 |
| AZZ-902 (aged) | alanine | 1:2 | 163784 |
| AZZ-902 (aged) | alanine | 1:3 | 75496 |
| AZZ-902 (aged) | threonine | 1:2 | 181327 |
| AZZ-902 (aged) | threonine | 1:3 | 81474 |

In the absence of post-added amino acid, peak 1 area is dramatically increased after 2.5 months of aging, indicating the formation of large zirconium species. For this antiperspirant salt, post-added glycine (5% and 10%, corresponding to Zr/amino acid weight ratio of 1:2 and 1:3 respectively), was unable to completely prevent zirconium from polymerizing. However, relative to the aged sample, 5% and 10% post-added glycine prevented the formation of large zirconium species by 38% and 59% respectively. Both alanine and threonine were also effective in preventing zirconium polymerization. Like glycine, the protection of zirconium was dose dependent. Both alanine and threonine were more effective than glycine in inhibiting zirconium polymerization. In this Example 7, zirconium protection by amino acids follow the sequence: alanine>threonine>glycine.

Example 8

Figure 6:
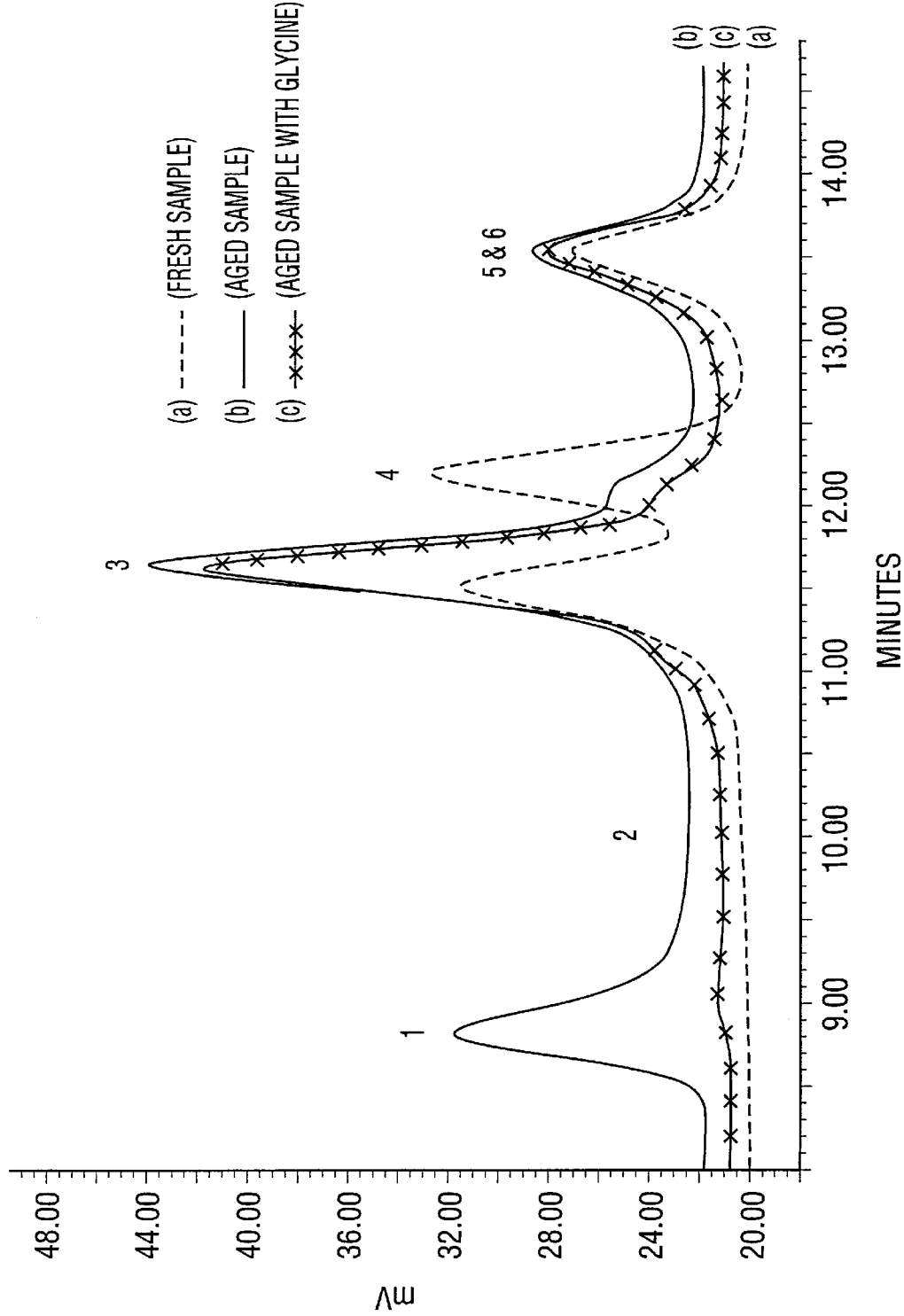
FIG. 6 shows GPC profiles for solutions of a ZAG of the type described in FIG. 1. Chromatogram (a) shows a GPC profile of a fresh solution of a ZAG. Chromatogram (b), shows the profile of a sample after 30 days of aging at room temperature. Chromatogram (c), shows the profile of a sample after 30 days of aging at room temperature with 5% post-added glycine (Zr:glycine ratio of 1:2).

The polymerization of zirconium species from an Q5-7167 AAZG (a ZAG as described above) solution with and without post-added glycine was examined. The Q5-7167 AAZG salt was made using the procedure documented in EP 0 653 203 A1 and the preparation and analyses of samples for GPC were done as described in Example 3. FIG. 6, chromatograms (a), (b) and (c) show GPC profiles for this ZAG (a) without aging, (b) after 30 days at room temperature and (c) after 30 days at room temperature with 5% post-added glycine. The corresponding areas of peaks 1 from the GPC profiles are shown in Table 5.

TABLE 5

| Sample | Chromatogram in FIG. 6 | Post-added amino acid | Zr/amino acid weight ratio | Peak 1 area |
| --- | --- | --- | --- | --- |
| Q5-7167 AAZG (no aging) | (a) | none | 1:1 | 9799 |
| Q5-7167 AAZG (30 days aging at room temperature) | (b) | none | 1:1 | 270938 |
| Q5-7167 AAZG (30 days aging at room temperature with 5% post added glycine) | (c) | glycine | 1:2 | 15776 |

The unaged sample showed a small peak 1 in the GPC profile, indicating the absence of large zirconium species and the presence of significant quantity of zirconium species less than 125 Å; this is consistent with the procedure described in EP 0 653 203 A1 for preparing a ZAG in which small zirconium species are enhanced. A significant increase in the area of peak 1 is noted, and, therefore, an increase in large zirconium species, after one month at room temperature. Thus, the procedure described in EP 0 653 203 A1 does not adequately address the polymerization of zirconium in solution. When 5% glycine is added to the Q5-7167 AAZG solution, peak 1 area drops significantly after 1 month at room temperature. Similar to the observations made above, post-added glycine stabilized the activated ZAG in solution.

Example 9

Stabilization of ZAG in a Gel Product by Post-added Amino Acids

Post-added glycine was used to stabilize ZAG in a gel product containing 3% glycine. Table 6 shows the composition of a typical gel product consisting of an organic phase and an aqueous phase using AZP-902 as the antiperspirant salt (Product A). An organic phase made by combining the following products from Dow Corning Corporation, Midland, Mich. in the amounts recited in Table 6 (cyclomethicone (and) dimethicone copolyol (DC3225C)+ dimethicone (DC200)+phenyl trimethicone (DC556)) (90.0 g) was placed in a 2 liter stainless steel container and 406.5 g of an aqueous phase (made by combining AZP-902 (46% solution) with and without glycine+SD alcohol 40+propylene glycol+tripropylene glycol+distilled water in the amounts described in Table 6) was added slowly with homogenization over a period of 1.0 hour at room temperature. At the end of this time, when the gel product was formed, 3.5 g of fragrance were added. The sample was further homogenized for an additional 10 minutes.

TABLE 6

| Ingredient | Gel Composition A (without glycine) | Gel Composition B (with glycine) |
| --- | --- | --- |
| Cyclomethicone (and) Dimethicone copolyol (DC3225C) | 9.00 | 9.00 |
| Dimethicone (DC200) | 7.25 | 7.25 |
| Phenyl trimethicone (DC556) | 1.75 | 1.75 |
| AZP-902 (46% solution) | 48.00 | 48.00 |
| Glycine | 0.00 | 3.00 |
| SD alcohol 40 | 8.00 | 8.00 |
| Propylene glycol | 4.00 | 4.00 |
| Tripropylene glycol | 7.00 | 7.00 |
| Distilled water | 14.30 | 11.30 |
| Fragrance | 0.70 | 0.70 |
| Total | 100.00 | 100.00 |

The ZAG salt contained 13–15% zirconium and 15% glycine; that is, the Zr/glycine ratio was approximately 1:1. A forty six percent solutions of the salt (46.0 g ZAG+54.0 g water) was prepared and 48.00 g of this solution was used in the product. Therefore, the percent of ZAG salt in the gel product was 22.0%. Also included in Table 6 is a gel product containing AZP-902 (product B), but with 3% of additional glycine; the Zr/glycine weight ratio in the product was 1:2. These samples were aged for 1 month at room temperature and 49 degrees C. (120 degrees F.) and GPC analysis was done on the extracted aqueous phases. For GPC analysis, 1–2 g samples were extracted with 5 ml toluene with shaking for 5 minutes to remove the organic phase. The organic extract was discarded and 1.0 g portions of the aqueous phase were diluted to approximately 10% of the ZAG salt. GPC data for peak 1 for these samples are shown in Table 7. A 10% solution of pure AZP-902 was also injected for comparison of peak 1 areas with the extracted AZP-902 from the gels.

TABLE 7

| Sample | Zr/glycine ratio | Area Peak 1 (RT) | Area Peak 1 (49° C.) |
| --- | --- | --- | --- |
| AZP-902 (no aging) | 1:1 | 10022 | 10022 |
| AZP-902 extracted from aged Gel Product A | 1:1 | 62348 | 238142 |
| AZP-902 extracted from aged Gel Product B | 1:2 | 9024 | 9892 |

In the absence of glycine, the area of peak 1 for the Gel Product A increased about six-fold relative to a fresh solution of AZP-902, after aging at room temperature, indicating formation of large zirconium species. However, in the presence of post-added glycine the area of peak 1 for Gel Product B (Zr/glycine ratio=1:2) was significantly reduced; peak 1 area was constant relative to the unaged sample. The results show that post-added glycine can prevent the polymerization of zirconium in a gel product, similar to that observed in solutions (see above).

Increasing temperature is known to accelerate the polymerization of zirconium in aqueous solution of ZAG. After 30 days at 49 degrees C. (120 degrees F.), the zirconium peak area of Gel Product A increased about twenty-four-fold from baseline. Product B containing post-added glycine (Zr/glycine weight ratio=1:2) did not show an increase in peak 1 area after 30 days at 49 degrees C. (120 degrees F.). These results indicate that the effects of aging as reflected in an increase in larger zirconium species/decrease in smaller zirconium species may be reduced or eliminated by using the zirconium:amino acid ratios described for the invention either at room temperature or elevated temperature. Because of its availability, glycine is a convenient amino acid to use; however other water soluble amino acids may also be used. While various features of the invention have been described, it is also intended that further modifications customary to those skilled in the art may be made and still remain within the spirit and scope of the invention.

What is claimed is:

1. A stick cosmetic composition for reducing body malodor comprising:
   (a) an oil phase made by combining:
      1) 0.5–8.0% of a siloxane polyamide gelling agent;
      2) 20–60% of a silicone fluid selected from the group consisting of D4, D5 and D6 cyclomethicones and mixtures thereof where the D# represents the number of siloxane units in the ring;
      3) 0–20% of at least one cosmetic ingredient selected from the group consisting of C8–C22 fatty alcohols, C12–C36 fatty esters, C8–C18 alkyl benzoates, and linear polysiloxanes;
      4) 0–10% of a cosmetically acceptable surfactant selected from the group consisting of cationic surfactants, nonionic surfactants, anionic surfactants, amphoteric surfactants, dimethicone copolyols and polyether ethoxylates;
      5) 0–3% of a fragrance;
   (b) a polar phase made by combining:
      1) 5–40% of water and/or water miscible solvents;
      2) 1.5–20% of at least one amino acid selected from the group consisting of glycine, alanine, threonine and leucine;

3) 10–25% of a ZAG complex;
4) 0–5% of a cosmetically acceptable surfactant selected from the group consisting of cationic surfactants, nonionic surfactants, anionic surfactants, amphoteric surfactants, dimethicone copolyols and polyether ethoxylates.

2. A stick cosmetic composition according to claim 1 wherein the stick cosmetic composition is an antiperspirant.

3. A stick cosmetic composition for reducing body malodor comprising:
   (a) an oil phase made by combining:
      1) 20–60% of a cosmetically acceptable solvent selected from the group consisting of C2–C8 polyhydric alcohols, C8–C22 unsaturated fatty alcohols, and branched and straight chain C8–C22 saturated fatty alcohols;
      2) 0–10% of a cosmetically acceptable surfactant selected from the group consisting of cationic surfactants, nonionic surfactants, anionic surfactants, amphoteric surfactants, dimethicone copolyols and polyether ethoxylates;
      3) 0–3% of a fragrance;
      4) 5–25% of a linoleic acid dimer based polyamide;
   (b) a polar phase made by combining:
      1) 5–40% of water and/or water miscible solvents;
      2) 1.5–20% of at least one amino acid selected from the group consisting of glycine, alanine, threonine and leucine;
      3) 10–25% of a ZAG complex;
      4) 0–5% of a cosmetically acceptable surfactant selected from the group consisting of cationic surfactants, nonionic surfactants, anionic surfactants, amphoteric surfactants, dimethicone copolyols and polyether ethoxylates.

4. A stick cosmetic composition according to claim 3 wherein the stick cosmetic composition is an antiperspirant.

5. A gel cosmetic composition for reducing body malodor comprising:
   (a) an oil phase made by combining:
      1) 12–20% cyclomethicone;
      2) 0.5–2% dimethicone copolyol;
      3) 5–20% linear silicones;
   (b) a polar phase made by combining:
      1) 35–70% water;
      2) 5–40% water miscible solvents;
      3) 1.5–20% of at least one amino acid selected from the group consisting of glycine, alanine, threonine and leucine;
      4) 10–25% of a ZAG complex;
      5) 0–2% of a cosmetically acceptable surfactant selected from the group consisting of cationic surfactants, nonionic surfactants, anionic surfactants, amphoteric surfactants, dimethicone copolyols and polyether ethoxylates.

6. A gel cosmetic composition according to claim 5 wherein the gel cosmetic composition is an antiperspirant.

7. A cream cosmetic composition for reducing body malodor comprising:
   (a) an oil phase made by combining:
      1) 2–10% cyclomethicone;
      2) 0.1–3% of mon-, di-, or triglycerides and mixtures thereof;
      3) 4–15% of a cosmetically acceptable surfactant selected from the group consisting of cationic surfactants, nonionic surfactants, anionic surfactants, amphoteric surfactants, dimethicone copolyols and polyether ethoxylates;
      4) 3–8% (preferably 3.5–6.5%) of a C8–C22 fatty alcohol;
   (b) a polar phase made by combining:
      1) 40–89% water;
      2) 1.5–20% of at least one amino acid selected from the group consisting of glycine, alanine, threonine and leucine;
      3) 10–25% of a ZAG complex.

8. A cream cosmetic composition according to claim 7 wherein the cream cosmetic composition is an antiperspirant.

9. A spray cosmetic composition for reducing body malodor made by combining:
   a) 35–87% water;
   b) 3–7% water soluble emollient;
   c) 0.5–3% of a cosmetically acceptable surfactant selected from the group consisting of cationic surfactants, nonionic surfactants, anionic surfactants, amphoteric surfactants, dimethicone copolyols and polyether ethoxylates;
   d) 10–25% of a ZAG;
   e) 1.5–20% of at least one amino acid selected from the group consisting of glycine alanine, threonine and leucine.

10. A spray cosmetic composition according to claim 9 wherein the spray cosmetic composition is an antiperspirant.

11. A roll-on cosmetic composition for reducing body malodor made by combining:
   a) 27–89% water;
   b) 0.5–3% magnesium aluminum silicate;
   c) 0.5–10% of a cosmetically acceptable surfactant selected from the group consisting of cationic surfactants, nonionic surfactants, anionic surfactants, amphoteric surfactants, dimethicone copolyols and polyether ethoxylates;
   d) 0–5% of water miscible solvent(s);
   e) 10–25% of a ZAG;
   f) 1.5–20% of at least one amino acid selected from the group consisting of glycine alanine, threonine and leucine.

12. A roll-on cosmetic composition according to claim 11 wherein the roll-on cosmetic composition is an antiperspirant.

13. A water-in-silicone roll-on cosmetic composition for reducing body malodor comprising:
   (a) an oil phase made by combining:
      1) 20–50% cyclomethicone;
      2) 0.5–2% dimethicone copolyol;
   (b) a polar phase made by combining:
      1) 30–50% water;
      2) 5–40% water miscible solvents;
      3) 1.5–20% of at least one amino acid selected from the group consisting of glycine alanine, threonine and leucine;
      4) 10–25 of a ZAG complex;
      5) 0–2% of a cosmetically acceptable surfactant selected from the group consisting of cationic surfactants, nonionic surfactants, anionic surfactants, amphoteric surfactants, dimethicone copolyols and polyether ethoxylates.

14. A water-in-silicone roll-on cosmetic composition according to claim 13 wherein the water-in-silicone roll-on cosmetic composition is an antiperspirant.

* * * * *